US008741322B2

(12) United States Patent
Aubrun-Sonneville et al.

(10) Patent No.: US 8,741,322 B2
(45) Date of Patent: Jun. 3, 2014

(54) WATER OIL-IN-WATER EMULSION

(75) Inventors: Odile Aubrun-Sonneville, Antony (FR);
Carole Guiramand, Jouy en Josas (FR)

(73) Assignee: L'Oreal, Paris (FR)

( * ) Notice: Subject to any disclaimer, the term of this patent is extended or adjusted under 35 U.S.C. 154(b) by 340 days.

(21) Appl. No.: 11/154,715

(22) Filed: Jun. 17, 2005

(65) Prior Publication Data

US 2005/0287104 A1    Dec. 29, 2005

Related U.S. Application Data

(60) Provisional application No. 60/587,854, filed on Jul. 15, 2004.

(30) Foreign Application Priority Data

Jun. 28, 2004 (FR) ...................... 0451342

(51) Int. Cl.
    *A61K 8/02*      (2006.01)
    *A61K 31/00*      (2006.01)

(52) U.S. Cl.
    USPC ........................... 424/401; 424/78.2

(58) Field of Classification Search
    USPC ......................................... 424/401
    See application file for complete search history.

(56) References Cited

U.S. PATENT DOCUMENTS

| | | | | |
|---|---|---|---|---|
| 4,304,563 A * | 12/1981 | Grollier et al. | ............... | 8/127.51 |
| 5,498,406 A | 3/1996 | Nearn et al. | | |
| 6,033,051 A * | 3/2000 | Kaneko | ............ | 347/23 |
| 6,039,936 A * | 3/2000 | Restle et al. | ................. | 424/70.1 |
| 6,280,765 B1 * | 8/2001 | Gueret | ......................... | 424/449 |
| 6,562,356 B2 * | 5/2003 | Verite et al. | ................... | 424/401 |
| 2003/0087967 A1 | 5/2003 | Quemin | | |
| 2003/0206955 A1 * | 11/2003 | Sonneville-Aubrun et al. | ............... | 424/486 |
| 2005/0226842 A1 | 10/2005 | Douin et al. | | |

FOREIGN PATENT DOCUMENTS

| | | |
|---|---|---|
| EP | 1 120 101 | 8/2001 |
| EP | 1 120 102 | 8/2001 |
| EP | 1160005 A1 * | 12/2001 |
| FR | 2 755 849 | 5/1998 |
| FR | 2 809 010 | 11/2001 |
| WO | WO 02/056843 | 7/2002 |
| WO | WO 02/064107 | 8/2002 |

OTHER PUBLICATIONS

Flick, Cosmetic Additives- An Industrial Guide, 1991, p. 215 and 742.*
Geerat et al. Capillary GC of triglycerides in fats and oils using a high temperature phenylmethylsilicone stationary phase. Part II. The analysis of chocolate fats; Journal of the American Oil Chemists' Society, vol. 64, No. 1 / Jan. 1987, p. 100-105.*
U.S. Appl. No. 11/154,675, filed Jun. 17, 2005, Guiramand, et al.
U.S. Appl. No. 11/213,915, filed Aug. 30, 2005, Guiramand.
Notice of Reasons for Rejection for Japanese Application 2005-187147, Drafted Feb. 14, 2007, Mailed Feb. 20, 2007, 3 pp.

* cited by examiner

*Primary Examiner* — Layla Soroush
(74) *Attorney, Agent, or Firm* — Oblon, Spivak, McClelland, Maier & Neustadt, L.L.P.

(57) ABSTRACT

The present invention relates to a composition preferably useful for topical application containing, or in the form of, a fine oil-in-water emulsion, to the process for preparing it and to its use especially for treating, caring for, making up and/or cleansing the skin, the integuments (hair, eyelashes or nails) and/or mucous membranes. In a preferred embodiment the invention emulsion is obtained without the input of energy. The composition may especially be a cosmetic and/or dermatological composition.

16 Claims, No Drawings

WATER OIL-IN-WATER EMULSION

REFERENCE TO PRIOR APPLICATIONS

This application claims priority to U.S. provisional application 60/587,854 filed Jul. 15, 2004, and to French patent application 0451342 filed Jun. 28, 2004, both incorporated herein by reference.

FIELD OF THE INVENTION

The present invention relates to a composition preferably useful for topical application comprising, or in the form of, a fine oil-in-water emulsion, to the process for preparing it and to its use especially for treating, caring for, making up and/or cleansing the skin, the integuments (hair, eyelashes or nails) and/or mucous membranes. In a preferred embodiment the invention emulsion is obtained without the input of energy. The composition may especially be a cosmetic and/or dermatological composition.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

For various reasons associated in particular with better comfort of use (softness, emollience and the like), current cosmetic or dermatological compositions are usually in the form of an emulsion of the oil-in-water (O/W) type, i.e. a support consisting of an aqueous dispersing continuous phase and an oily dispersed discontinuous phase. These O/W emulsions are more in demand than emulsions of the water-in-oil (O/W) type, which consist of a fatty dispersing continuous phase and of an aqueous dispersed discontinuous phase, since they give the skin on application a softer, less greasy and lighter feel than the W/O emulsion systems.

Moreover, in cosmetics, dermatology and pharmacy, emulsions comprising small globules (or droplets) of the dispersed phase, also known as fine emulsions, are often desired, whether:
  for their texture: the compositions may be more or less viscous and may range from the consistency of a lotion to that of a cream;
  for their visual appearance, which may range from a transparent or opalescent composition to a white composition;
  for their cosmetic feel that especially promotes their speed of penetration;
  for their broad possible positioning in market terms, since such compositions satisfy consumers in both Europe and Japan and in other countries.

In the present patent application, the term "fine emulsion" means an emulsion in which the size of the globules of the dispersed phase ranges from 50 to 500 nanometers.

In terms of technology, at the present time, to obtain fine O/W emulsions of this type, energy needs to be supplied to the mixture, either large mechanical energy in order to fragment the dispersed phase into fine globules, or thermal energy by proceeding via a process of change of phase with temperature (80° C.), for instance the systems prepared by the PIT "Phase Inversion Temperature" technique. These systems are well known and nowadays allow access to fine emulsions.

Thus, the technique of mechanical input of energy makes it possible to obtain fine transparent emulsions, also known as (nanoemulsions), described, for example, in documents EP-A-728 460, EP-A-780 114, EP-A-780 115, EP-A-879 589, EP-A-1 010 413, EP-A-1 010 414, EP-A-1 010 415, EP-A-1 010 416, EP-A-1 013 338, EP-A-1 016 453, EP-A-1 018 363, EP-A-1 020 219, EP-A-1 025 898, EP-A-1 120 102, EP-A-1 120 101, EP-A-1 160 005, EP-A-1 172 077 and EP-A-1 353 629. The oil globules of the nanoemulsions have a mean size of less than 100 nm. The drawback of these nanoemulsions is the need for large input of mechanical energy.

Nanoemulsions are also described in the publications by Forgiarini, J. Esquena, C. Gonzàlez and C. Solans, "Formation of Nano-emulsions by Low Energy Emulsification. Methods at Constant Temperature", Langmuir, 2001, 17, 2076-2083H., and Forgiarini, J. Esquena, C. Gonzàlez and C. Solans, "Studies of the Relation Between Phase Behavior and Emulsification Methods with Nanoemulsion Formation", Prog. Colloid Polym Sci., 2000, 115 (Trends in Colloid and Interface Science XIV), 36-39. These publications describe decane-in-water emulsions stabilized with a particular surfactant, laureth-4 (or Brij 30), and prepared by addition of water to a decane/Brij 30 mixture. The surfactant comprises a short (C12) alkyl chain, which makes it more irritant than its homologues with a longer alkyl chain. Moreover, the emulsions described in these documents are unstable, especially at the microscopic level (drop diameter) and are consequently too unstable for industrial application.

Moreover, the PIT technique is, in its principle, well known to those skilled in the art and is especially described in the articles "Phase Inversion Emulsification" by Th Farster et al, published in Cosmetics & Toiletries, vol. 106, December 1991, pp. 49-52, "Application of the phase-inversion-temperature method to the emulsification of cosmetics", by T. Mitsui et al., published in American Cosmetics and Perfumery, vol. 87, December 1972, and in documents WO-A-89/11907, DE-A-4 318 171, EP-A-815 846 and EP-A-1 297 824.

However, these techniques for obtaining fine emulsions have the following drawbacks:
  The high temperature of the PIT process imposes formulation constraints. Thus, it is difficult to use this technique with heat-sensitive molecules with low flashpoints, and the technique is thus limited to heat-insensitive molecules with high flashpoints. This restricts the type and number of starting materials that may be used, or alternatively, if it is desired to use, for example, molecules with low flashpoints, it is necessary, as a function of these starting materials, to adapt the procedure and these emulsions then become more complex and more expensive to obtain. As a result, this process excludes or at the very least limits the use of volatile compounds such as volatile lipophilic compounds, especially volatile oils, for instance volatile silicones, and certain heat-sensitive active agents or plant extracts.
  High-pressure or very high-pressure homogenizers, which allow fine emulsions to be prepared by input of energy, are expensive and fragile items of equipment, which thus generate large industrial implementation costs.

Moreover, transparent microemulsions are known in the prior art. Microemulsions are not strictly speaking emulsions, in contrast with nanoemulsions; they are transparent solutions of micelles swollen with oil, this oil generally being of very short chain length (e.g.: hexane or decane) and moreover being dissolved by means of the combined presence of a large amount of surfactants and cosurfactants forming the micelles. The swollen micelles are very small on account of the small amount of oil they are capable of dissolving. This very small size of the micelles is the reason for their transparency. However, unlike the nanoemulsions described above, microemulsions are formed spontaneously by mixing the constituents together, without any input of mechanical energy other than simple magnetic stirring, and irrespective of the order of addition of the constituents. In addition, they are thermodynamically stable systems. The major drawbacks of microemulsions are associated with their high proportion of surfactants relative to the oil, leading to intolerance and resulting in a tacky feel when applied to the skin. Moreover, the microemulsion state of the system is defined by the choice of constituents and their relative proportions, and also the temperature, as shown by the phase diagram presented in FIG. 11.7 of the article "The colloidal domain", D. F. Evans, H. Wennerström, published by Wiley-VCH (1999). For the description of microemulsions, reference may be made, for example, to the article by M. Bourrel and R. S. Schechter "Microemulsions and related systems", pages 25 to 30, published by Marcel Dekker, 1988. These microemulsions are therefore not fine emulsions and cannot overcome the drawbacks of the fine emulsions described above.

There is thus still a need to prepare fine O/W emulsions which remain stable when they are diluted and which are obtained via less expensive and less complex processes than those of the prior art, i.e. processes not requiring any energy input, whether this energy is mechanical or thermal, and thus without proceeding via high temperatures or without equipment that inputs a large amount of energy, these processes having no effect on the chemical stability of the compounds constituting the composition.

SUMMARY OF THE INVENTION

The inventors have found, surprisingly, that it is possible to prepare fine emulsions without any energy input and prepared entirely at room temperature if desired, by means of a particular choice of surfactants, a particular choice of oils, and a given oil/surfactant ratio.

DETAILED DESCRIPTION OF THE PREFERRED EMBODIMENTS

One subject of the present invention is thus a composition for topical application, comprising or in the form of an oil-in-water emulsion, the oil-in-water emulsion comprising an oily phase dispersed in an aqueous phase, the globules of oily phase having a mean diameter ranging from 50 to 500 nm, wherein:
it contains an emulsifying system containing (i) at least one nonionic surfactant with a melting point of less than 45° C. and an HLB ranging from 10 to 15, the surfactant comprising a polar portion comprising at least 5 oxyethylene groups and an apolar portion comprising at least one branched or unsaturated alkyl chain containing from 14 to 22 carbon atoms, and (ii) at least one anionic surfactant,
the oily phase contains oily constituents including at least one hydrocarbon-based oil with a molecular weight of greater than or equal to 400, the amount of hydrocarbon-based oils with a molecular weight of greater than or equal to 400 representing at least 25% by weight relative to the total weight of the oily phase and the amount of triglyceride-based oils representing less than 15% by weight relative to the total weight of the oily phase, at least one hydrocarbon-based oil with a molecular weight of greater than or equal to 400 being chosen from alkanes with a melting point of less than 45° C.,
the weight ratio of the amount of oily constituents of the oily phase to the amount of emulsifying system ranges from 0.8 to 3.5.

The term "topical application" means herein an external application to keratin materials, especially the skin, the scalp, the eyelashes, the eyebrows, the nails, the hair and/or mucous membranes. Since the composition is preferably intended for topical application, it preferably comprises a physiologically acceptable medium. The term "physiologically acceptable medium" means a medium that is compatible with the skin, the lips, the scalp, the eyelashes, the eyes, the nails and/or the hair. The composition may especially constitute a cosmetic or dermatological composition.

In the present patent application, the term "amount of oily constituents of the oily phase" means the total amount of oils and of other fatty substances present in the oily phase, i.e. the amount of constituents of the oily phase other than the emulsifying system especially comprising the surfactants and cosurfactants.

According to one important characteristic of the compositions in accordance with the present invention, the mean diameter of the globules (or droplets) of oily phase dispersed in the dispersing aqueous phase ranges from 50 to 500 nm, preferably from 50 nm to 250 nm and more particularly from 80 to 200 nm, this mean diameter being a mean intensity diameter, measured by quasi-elastic light scattering, for example with the machine Model BI-90 from the company Brookhaven Instruments Corporation.

According to the size of the globules of the oily phase, the visual appearance of the composition according to the invention ranges from transparent to a white appearance, passing through opalescent.

The emulsions according to the invention have the advantage of being able to be prepared at room temperature and thus via a process that does not degrade the constituents of the composition (active agents in particular), and which, also, is relatively inexpensive, relatively simple and imposes no constraints since no energy is required to obtain this system. The emulsions according to the invention furthermore have the advantage of being entirely stable over time and at temperature, since no creaming (i.e. rising of the oil globules), no sedimentation (i.e. collection of the oil globules at the bottom of the container) and no phase separation (i.e. separation of the aqueous and oily phases) is observed over time and at various storage temperatures (4° C., 25° C. and 45° C.). The emulsions according to the invention also have the advantage of being able to be in very varied form, i.e. by having a wide range of textures in terms of viscosity, feel (for example as a function of the oil content), which makes it possible to offer them to consumers who have widely differing habits and sensitivities.

The compositions according to the invention may be more or less viscous and may have an appearance ranging from a lotion (fluid product) to a cream (thick product). Thus, their viscosity may range, for example, from 1 cpoise (1 mPa·s) to 20 000 cpoises (20 000 mPa·s), this viscosity being measured after 10 minutes of shear, using a Rheomat 180 viscometer at a shear rate of 200 rpm, with a rotor adapted to the viscosity of the composition.

Emulsifying System

The composition according to the invention comprises an emulsifying system comprising (i) at least one nonionic surfactant and (ii) at least one anionic surfactant. In this emulsifying system, preferably the nonionic surfactant is generally introduced into the oily phase while the anionic surfactant may be introduced either into the aqueous phase or into the oily phase.

The emulsifying system may for example be present in an amount ranging from 0.6% to 11% by weight and preferably from 1.1% to 9% by weight relative to the total weight of the composition.

1. Nonionic Surfactant

The nonionic surfactants used in the composition of the invention preferably have a melting point of less than 45° C. and are therefore liquid at a temperature below 45° C., and in particular they preferably are liquid at a temperature ranging from 20 to 44° C. They preferably have an HLB ranging from 10 to 15 and they comprise a polar portion comprising at least 5 oxyethylene groups and an apolar portion comprising at least one branched or unsaturated alkyl chain, containing from 14 to 22 carbon atoms.

The HLB (hydrophilic-lipophilic balance) of an emulsifying surfactant is calculated according to the following formula:

$$HLB = 20 \times \frac{\text{hydrophilic } m}{\text{total } m \text{ of the } SA}$$

in which hydrophilic m represents the weight of the hydrophilic group (i.e. the polar portion) and total m of the SA represents the total weight of the surfactant.

According to one preferred embodiment of the invention, the nonionic surfactants are chosen from fatty acid esters of polyethylene glycol, oxyethylenated fatty acid esters of polyol and oxyethylenated fatty alcohol ethers, and mixtures thereof. These oxyethylenated surfactants comprise at least 5 oxyethylene groups; they may comprise, for example, from 5 to 21 oxyethylene groups and preferably from 5 to 18 oxyethylene groups.

Examples of fatty acid esters of polyethylene glycol that may be mentioned include PEG-8 isostearate (or polyethylene 400 isostearate) such as the product sold under the name Prisorine 3644 by the company Uniqema, PEG-10 isostearate, PEG-12 isostearate and PEG-15 isostearate, and mixtures thereof.

Oxyethylenated fatty acid esters of polyol that may especially be mentioned include oxyethylenated fatty acid esters of glycerol, oxyethylenated fatty acid esters of sorbitol, for instance PEG-15 glyceryl isostearate such as the product sold under the name Oxypon 2145 by the company Zschimmer Schwarz, and PEG-20 sorbitan triisostearate, and mixtures thereof.

An example of an oxyethylenated fatty alcohol ether that may be mentioned is isosteareth-10 such as the product sold under the name Arosurf 66E10 by the company Witco.

A mixture of the surfactants mentioned above may be used.

The amount of nonionic surfactant(s) as defined above may range, for example, from 0.5% to 10% by weight and preferably from 1% to 8% by weight relative to the total weight of the composition.

2. Anionic Surfactant

The anionic surfactants may preferably be chosen from the group formed by:
  alkaline salts of dicetyl and of dimyristyl phosphate;
  alkaline salts of cholesteryl sulfate;
  alkaline salts of cholesteryl phosphate;
  acylamino acid (or lipoamino acid) salts such as monosodium and disodium acylglutamates, for instance the disodium salt of N-stearoyl-L-glutamic acid sold under the name Acylglutamate HS21 by the company Ajinomoto;
  the sodium salts of phosphatidic acid;
  alkyl sulfate and alkylsulfonate derivatives;
  and mixtures thereof.

According to one preferred embodiment of the invention, the anionic surfactant used is an acylamino acid salt such as monosodium and disodium acylglutamate, for instance the disodium salt of N-stearoyl-L-glutamic acid sold under the name Acylglutamate HS21 by the company Ajinomoto.

Mixtures may be used.

The anionic surfactants may for example be present in the emulsion of the invention in an amount preferably ranging from 0.05% to 2% by weight and more particularly from 0.1% to 1% by weight relative to the total weight of the composition.

3. Cosurfactants

The emulsifying system may also comprise one or more cosurfactants, which are surfactants with an HLB of less than 5. These cosurfactants have a melting point of less than or equal to 45° C. and are therefore liquid at a temperature of less than or equal to 45° C.; they are especially liquid at a temperature of from 20 to 45° C. Examples of cosurfactants that may be mentioned include fatty alcohols such as isostearyl alcohol and oleyl alcohol; glycerol esters of fatty alcohol, such as glyceryl isostearate; sorbitan esters of fatty alcohol, for instance sorbitan isostearate. The amount of cosurfactants may range, for example, from 0.005% to 5% by weight and preferably from 0.01% to 2% by weight relative to the total weight of the composition. Mixtures may be used.

Oily Phase

The oily phase comprises oily constituents, and it should comprise at least one hydrocarbon-based oil with a molecular weight of greater than or equal to 400, the amount of hydrocarbon-based oils with a molecular weight of greater than or equal to 400 preferably representing at least 25% by weight relative to the total weight of the oily phase, for example from 25% to 100% by weight of the oily phase, better still from 25% to 80% by weight and even better still from 30% to 70% by weight of the oily phase.

Moreover, the oily phase should preferably contain less than 15% by weight of triglyceride-based oils relative to the total weight of the oily phase.

Furthermore, at least one hydrocarbon-based oil with a molecular weight of greater than or equal to 400 must be chosen from alkanes with a melting point of less than 45° C.

In the present patent application, the term "hydrocarbon-based oil" means an oil essentially formed from, or even consisting of, carbon and hydrogen atoms, and possibly oxygen and nitrogen atoms, and not containing any silicon or fluorine atoms. Such an oil may contain ester, ether, amine or amide groups. The hydrocarbon-based oils with a molecular weight of greater than or equal to 400 used according to the invention are chosen from alkanes with a melting point of less than 45° C., fatty acid esters, fatty alcohol ethers, and mixtures thereof. Hydrocarbon-based oils with a molecular weight of greater than or equal to 400 that may be mentioned in particular include jojoba oil; fatty acid esters such as isocetyl palmitate and isocetyl stearate; oils of plant origin; fatty alcohol ethers such as diisostearyl ether.

Alkanes with a melting point of less than 45° C. that may especially be mentioned include hydrogenated polyisobutene such as Parleam® oil and liquid petroleum jelly, and mixtures thereof. According to a particular embodiment of the invention, the amount of alkanes with a melting point of less than 45° C. may represent from 25% to 100% by weight of the oily phase, better still from 25% to 80% by weight and even better still from 30% to 70% by weight of the oily phase.

The triglyceride-based oils generally have a molecular weight of greater than 400. However, to achieve the aim of the invention, the amount of these oils should preferably be limited to less than 15% by weight and preferably to less than 10% by weight relative to the total weight of the oily phase, the oily phase comprising, as indicated above, the oily constituents without the surfactants of the emulsifying system. Triglyceride-based oils that may be mentioned include oils of plant origin such as sweet almond oil, avocado oil, castor oil, olive oil, sesame seed oil, groundnut oil, grapeseed oil, rapeseed oil, coconut oil, hazelnut oil, shea butter, palm oil, apricot kernel oil, beauty-leaf oil, rice bran oil, corn germ oil, wheat germ oil, soybean oil, sunflower oil, evening primrose oil, safflower oil, passion flower oil and rye oil.

In addition to the hydrocarbon-based oils with a molecular weight of greater than or equal to 400, the oily phase may also contain one or more oils with a molecular weight of less than 400, chosen, for example, from silicone oils or hydrocarbon-based oils with a molecular weight of less than or equal to 400. Silicone oils that may especially be mentioned include cyclic or linear silicone oils, especially those having a viscosity of less than or equal to 10 centistokes at 25° C., for instance cyclopolydimethylsiloxanes (cyclomethicones) such as cyclopentasiloxane and cyclohexadimethylsiloxane. Examples of hydrocarbon-based oils with a molecular weight of less than 400 that may be mentioned include isoparaffins such as isododecane (molecular weight: 194), isohexadecane (molecular weight: 258), dioctylcyclohexane; fatty acid esters, for instance isopropyl myristate, isopropyl palmitate, ethylhexyl palmitate, isostearyl neopentanoate and isononyl isononanoate (molecular weight: 320); fatty ethers such as dicaprylyl ether.

The amount of oily phase may range, for example, from 0.5% to 55% by weight relative to the total weight of the composition, preferably from 1% to 40% by weight, better still from 2% to 40% by weight and even better still from 5% to 30% by weight relative to the total weight of the composition.

In the composition according to the invention, the weight ratio of the amount of oily constituents of the oily phase to the amount of emulsifying system preferably ranges from 0.8 to 3.5 and preferably from 0.7 to 3. As indicated above, the amount of oily constituents of the oily phase corresponds to the total amount of oils and other fatty substances present in the oily phase, i.e. the amount of constituents of the oily phase other than the surfactants and/or cosurfactants forming part of the emulsifying system.

Aqueous Phase

The dispersing aqueous phase comprises water and may be, for example, a mixture of water and hydrophilic compound(s), especially such as polyhydric alcohols, for instance glycerol, propylene glycol, dipropylene glycol and sorbitol, water-soluble lower alcohols such as ethanol, isopropanol or butanol. In addition, it can, of course, contain water-soluble or water-dispersible adjuvants, and in particular the cosmetic and/or dermatological water-soluble adjuvants.

The aqueous phase may preferably represent from 45% to 99.5% by weight relative to the total weight of the composition, preferably from 60% to 99% by weight relative to the total weight of the composition and better still from 60% to 98% by weight relative to the total weight of the composition.

Adjuvants

Included among the adjuvants that may be contained in the aqueous phase and/or in the oily phase of the emulsions in accordance with the invention (according to their water-soluble or liposoluble nature), mention may be made especially of ionic or nonionic thickeners, antioxidants, emollients, cosmetic or dermatological active agents, fragrances, preserving agents, fillers, sequestering agents, pigments, dyes or any other ingredient usually used in the fields under consideration.

Needless to say, a person skilled in the art will preferably take care to select the optional compound(s) to be added to the composition according to the invention and the amounts thereof such that the advantageous properties intrinsically associated with the composition in accordance with the invention are not, or are not substantially, adversely affected by the envisaged addition.

Examples of active agents that may be mentioned include:
moisturizers, for instance sodium lactate; polyols, and in particular glycerol, sorbitol and polyethylene glycols; mannitol; amino acids; hyaluronic acid; lanolin; urea and mixtures containing urea, such as NMF (Natural Moisturizing Factor); petroleum jelly; N-lauroylpyrrolidonecarboxylic acid and its salts; essential fatty acids; essential oils; and mixtures thereof;

anti-ageing active agents and keratolytic agents such as α-hydroxy acids and especially acids derived from fruit, for instance glycolic acid, lactic acid, malic acid, citric acid, tartaric acid and mandelic acid, derivatives thereof, and mixtures thereof; β-hydroxy acids, for instance salicylic acid and its derivatives such as 5-n-octanoylsalicylic acid or 5-n-dodecanoylsalicylic acid; α-keto acids, for instance ascorbic acid or vitamin C and its derivatives such as its salts, for instance sodium ascorbate and magnesium or sodium ascorbyl phosphate; its esters, for instance ascorbyl acetate, ascorbyl palmitate and ascorbyl propionate, or its sugars, for instance glycosylated ascorbic acid, and mixtures thereof; β-keto acids; retinoids, for instance retinol (vitamin A) and its esters, retinal, retinoic acid and its derivatives, and also the retinoids described in documents FR-A-2 570 377, EP-A-199 636, EP-A-325 540 and EP-A-402 072; adapalene; carotenoids; and mixtures thereof;

vitamins, for instance vitamins A and C mentioned above, and also vitamin E (tocopherol) and its derivatives; vitamin B3 (or vitamin PP or niacinamide) and its derivatives; vitamin B5 (or panthenol or panthenyl alcohol or 2,4-dihydroxy-N-(3-hydroxypropyl)-3,3-dimethylbutanamide), in its various forms: D-panthenol, DL-panthenol), and derivatives and analogues thereof, such as calcium panthotenate, panthetine, pantotheine, ethyl panthenyl ether, pangamic acid, pyridoxine, pantoyl lactose and natural compounds containing it such as royal jelly; vitamin D and its analogues such as those described in document WO-A-00/26167; vitamin F or its analogues such as mixtures of unsaturated acids containing at least one double bond and especially mixtures of linoleic acid, of linolenic acid and of arachidonic acid, or compounds containing them;

antibacterial agents and anti-seborrhoeic agents such as salicylic acid, 2,4,4'-trichloro-2'-hydroxydiphenyl ether (or triclosan), 3,4,4'-trichlorobanilide (or triclocarban), azelaic acid, benzoyl peroxide and zinc salts, for instance zinc lactate, zinc gluconate, zinc pidolate, zinc carboxylate, zinc salicylate and/or zinc cysteate.

Thickeners that may especially be mentioned include thickening polymers, in particular:

carboxyvinyl polymers, such as the products sold under the names Carbopol (INCI name: carbomer) by the company Noveon; polyacrylates and polymethacrylates such as the products sold under the names Lubrajel and Norgel by the company Guardian or under the name Hispagel by the company Hispano Chimica;

polyacrylamides;

optionally crosslinked and/or neutralized 2-acrylamido-2-methylpropanesulfonic acid polymers and copolymers, for instance the poly(2-acrylamido-2-methylpropanesulfonic acid) sold by the company Clariant under the name Hostacerin AMPS (INCI name: ammonium polyacryldimethyltauramide), or such as crosslinked copolymers of acrylamide and of AMPS, in the form of a W/O emulsion, such as those sold under the name Sepigel 305 (INCI name: polyacrylamide/C13-14 isoparaffin/laureth-7) and under the name Simulgel 600 (INCI name: acrylamide/sodium acryloyldimethyl taurate copolymer/isohexadecane/polysorbate 80) by the company SEPPIC. Mention may also be made of crosslinked or linear AMPS polymers comprising a hydrophobic portion, such as the products sold under the names Aristoflex SNC, LNC and HMS by the company Clariant;

polysaccharides, for instance xanthan gum, guar gum and its derivatives such as hydroxypropyl guar, in particular the product sold under the name Jaguar HP105 by the company Rhodia, locust bean gum, acacia gum, scleroglucans, chitin and chitosan derivatives, carrageenans, gellans, alginates, celluloses such as microcrystalline cellulose, carboxymethylcellulose, hydroxymethylcellulose, hydroxypropylcellulose and hydroxyethylcellulose, for instance the product sold under the name Natrosol 250HHR by the company Aqualon;

nonionic polymers comprising at least one hydrophobic block and at least one hydrophilic block, such as the polyurethanes sold under the names Serad FX1010, Serad FX1100 (INCI name: steareth-100/PEG-136/HMDI copolymer) and Serad FX1035 by the company Hüls, those sold under the names Rheolate 255, Rheolate 278 and Rheolate 244 by the company Rheox (INCI name: polyether-urea-polyurethane), those sold under the names DW 1206F, DW 1206J, DW 1206B and DW 1206G by the company Röhm & Haas (INCI name: polyurethane), and the product sold under the name Acrysol RM 2020 by the company Röhm & Haas. Mention may also be made of aqueous solutions of copolymer of SMDI and fatty alcohol, sold under the names Aculyn 46 (INCI name: PEG-150 stearyl alcohol/SMDI polymer) and Aculyn 44 (INCI name: PEG-150 decyl alcohol/SMDI polymer) by the company Röhm & Haas;

anionic polymers comprising at least one hydrophobic chain, and especially acrylic or methacrylic polymers or copolymers (including terpolymers) comprising at least one hydrophobic chain, such as the copolymers obtained by copolymerization of acrylic or methacrylic acid or esters thereof with an ethylenically unsaturated monomer comprising a hydrophobic group, for instance the crosslinked copolymers sold under the names Pemulen TR1, Pemulen TR2 or Carbopol 1382 (INCI name: acrylates/C10-30 alkyl acrylate crosspolymer) by the company Noveon; the methacrylic acid/methyl acrylate/dimethyl-meta-isopropenyl benzyl isocyanate ethoxylated terpolymer, as an aqueous 25% solution, sold under the name Viscophobe DB100 by the company Amerchol, the acrylic acid/monostearyl itaconate oxyethylenated (20 QE) copolymer as an aqueous 30% dispersion sold under the name Structure 2001 by the company National Starch, the acrylic acid/monocetyl itaconate ethoxylated (20 OE) copolymer as an aqueous 30% dispersion sold under the name Structure 3001 by the company National Starch, and the acrylic copolymer soluble in alkaline medium, as an aqueous 30% dispersion, sold under the name Aculyn 22 by the company Röhm & Haas;

cationic polymers containing at least one hydrophobic block and at least one hydrophilic block, such as polyquaternium-24, for instance the product sold under the name Quatrisoft LM200 by the company Amerchol;

crosslinked cationic polymers, for instance polyquaternium-37 sold under the names Salcare SC96 by the company Ciba and Synthalen CR by the company 3V Sigma.

A subject of the invention is also a process for preparing the above-described emulsions. The process preferably comprises:

(1) preparing the oily phase (A) containing the oil(s) and other fatty substances, and the emulsifying system, with stirring, the stirring being performed, for example, using a magnetic bar, at a temperature ranging from about 20° C. to 45° C., until a homogeneous phase is obtained, (2) introducing into phase (A) 0.1% to 3% by weight of water (phase B) relative to the total weight of the composition, and mixing until a homogeneous phase (C) is obtained, (3) adding to phase (C) 55% to 75% by weight of water (phase D) relative to the total weight of the composition, to obtain after mixing a homogeneous phase E, and (4) adding the rest of the constituents of the aqueous phase (phase F).

The stirring is preferably performed using a magnetic bar or any other stirring system that gives gentle and thus low-energy stirring, at a temperature possibly ranging from 20 to 45° C. The term "gentle stirring" means stirring performed at a shear rate of less than 1000 $s^{-1}$ and preferably less than 100 $s^{-1}$.

At the same time as the phase F, the fragrance(s) may optionally be added if they are in an amount of less than 0.4% of the total weight of the composition. If they are in larger amounts, the surplus relative to 0.4% is added to the oily phase. Thus, if the composition contains 1% of fragrance, 0.6% is in the oily phase and 0.4% is in the aqueous phase (F).

The compositions of the invention may be used in any general manner, for example on any keratin material, such as the skin, the scalp, the hair, the eyelashes, the eyebrows, the nails or mucous membranes. They may be used as skincare products, for example protective, medicated or care creams for the face, the hands or the body, for instance protective or care body milk for the skin, the scalp or mucous membranes, or such as hygiene products, for instance cleansing products for the skin or mucous membranes, or alternatively hair products or antisun products.

The compositions may also constitute makeup products for the skin and/or the hair, for example by incorporating pigments into the composition especially to constitute foundations.

A subject of the invention is also the cosmetic use of the composition as defined above as a skincare product, a hygiene product, a hair product, an antisun product and a makeup product.

Another subject of the invention is a cosmetic process for treating a keratin material, such as the skin, the scalp, the hair, the eyelashes, the eyebrows, the nails or mucous membranes, wherein a composition as defined above is applied to the keratin material.

Moreover, compositions according to the invention may also be used for the impregnation of water-insoluble substrates to constitute articles (such as wipes) for caring for, cleansing and/or removing makeup from the skin, the eyelashes and/or the lips. The water-insoluble substrate may comprise one or more layers and it may be chosen from the group comprising woven materials, nonwoven materials, foams, sponges, wadding, felts, balls or films. It may especially be a nonwoven substrate based on fibres of natural origin (flax, wool, cotton or silk) or of synthetic origin (cellulose derivatives, viscose, polyvinyl derivatives, polyesters, for instance polyethylene terephthalate, polyolefins, for instance polyethylene or polypropylene, polyamides, for instance nylon, and acrylic derivatives). The nonwovens are described in general in Riedel's "Nonwoven Bonding Methods & Materials". Nonwoven World (1987). These substrates are obtained according to the usual processes of the technique for preparing nonwovens. Preferably, the fluidity of the invention compositions are formulated to have the appropriate fluidity for ease in impregnation, etc.

When the substrate is a nonwoven, a thick nonwoven is preferably used, which does not roll up into a ball and which is solid enough not to disintegrate or to pill when applied to the skin. It should be absorbent, soft on at least one face for removing makeup in particular from the eyes. Examples of suitable nonwovens that may be mentioned include those sold under the names Ultraloft 15285-01, Ultraloft 182-008, Ultraloft 182-010 and Ultraloft 182-016 by the company BBA, Vilmed M1519 Blau, Vilmed M 1550 N and 112-132-3 by the company Freudenberg, the product sold under the name Norafin 11601-010B by the company Jacob Holm Industries, and the flocked nonwovens sold under the names Univel 109 and Univel 119 by the company Uni Flockage.

Moreover, this substrate may comprise one or more layers having identical or different properties and have elasticity and softness properties and other properties suitable for the desired use. The substrates may comprise, for example, two parts having different elasticity properties, as described in document WO-A-99/13861, or may comprise a single layer with different densities, as described in document WO-A-99/25318 or may comprise two layers of different textures as described in document WO-A-98/18441.

The compositions impregnated onto the substrate may contain any compound that is suitable for the desired aim, for example foaming surfactants to obtain cleansing wipes, or care active agents to obtain skincare wipes. They may also be used for making up the skin, for example by impregnating the wipe with a composition containing pigments and possibly constituting a foundation.

A subject of the invention is thus also an article obtained by impregnating a water-insoluble substrate with a composition as defined above.

A subject of the invention is also the use of the composition as defined above for the preparation of an article for caring for, removing makeup from, cleansing or making up the skin, the lips and/or the eyelashes.

The examples that follow illustrate the invention without being limiting in nature. The amounts therein are weight percentages. The compounds are indicated as the INCI name or as chemical names, depending on the case.

Examples 1 to 7 According to the Invention

|  |  | Example 1 | Example 2 | Example 3 | Example 4 | Example 5 | Example 6 | Example 7 |
|---|---|---|---|---|---|---|---|---|
| PEG-8 isostearate | A | 5.80 | 1.67 | 6.66 | 6.66 | 6.66 | 6.66 | 6.66 |
| Hydrogenated polyisobutene |  | 8.75 | 2.51 | 10 | 10 | 10 | 10 | 20 |
| Isocetyl stearate |  |  |  |  |  | 10 |  |  |
| Isononyl isononanoate |  |  |  |  |  |  | 10 |  |
| Jojoba oil |  |  |  |  | 10 |  |  |  |
| Cyclic silicone |  | 8.75 | 2.51 | 10 |  |  |  |  |
| Water | B | 2.18 | 0.63 | 2.48 | 2.48 | 2.48 | 2.48 | 2.48 |
| Water | D | 45.07 | 12.64 | 51.55 | 51.55 | 51.55 | 51.55 | 51.55 |
| Water | F | qs 100 | qs 100 | qs 100 | qs 100 | qs 100 | qs 100 | qs 100 |
| Preserving agent |  | 0.78 | 0.23 | 0.88 | 0.88 | 0.88 | 0.88 | 0.88 |
| Disodium stearoyl glutamate |  | 0.16 | 0.05 | 0.13 | 0.13 | 0.13 | 0.13 | 0.13 |
| Glycerol |  | 3 |  |  |  |  |  |  |
| Propylene glycol |  |  |  |  | 3 |  | 3 | 3 |
| Ethanol |  |  |  |  |  | 5 |  |  |
| Steareth-100/PEG-136/HMDI copolymer (Serad FX1100) |  | 0.40 |  |  |  |  |  | 0.40 |
| Fragrance |  | 0.10 | 0.10 | 0.10 | 0.10 | 0.10 | 0.10 | 0.10 |
| Diameter of the globules of the oily phase* | 24 h | 152 nm | 86 nm | 90 nm | 170 nm | 180 nm | 196 nm | 83.5 nm |
| Viscosity at 25° C. (Rheomat 180) |  | 370 centipoises | 1.1 centipoises | 8 centipoises | not measured | not measured | not measured | not measured |
| Visual appearance |  | white | opalescent | opalescent | white | white | white | opalescent |
| Stability after 15 days at different temperatures (4°, RT, 45° C.) |  | stable | stable | stable | determined for 2 months at 45° C.: stable | stable | stable | determined for 2 months at 45° C.: stable |

*diameter measured by quasi-elastic light scattering, the measurement being performed using a BI-90 machine from Brookhaven. For examples 1 and 7, the diameter of the globules of oily phase is measured before gelation with the polymer.

COMPARATIVE EXAMPLES

1) Comparative Example 8

|  |  | Example 8 |
|---|---|---|
| Polyglyceryl 10 isostearate |  | 6.66 |
| Hydrogenated polyisobutene |  | 10 |
| Cyclic silicone |  | 10 |
| Water | B | 2.48 |
| Water | D | 51.55 |
| Water | F | qs 100 |
| Preserving agent |  | 0.88 |
| Disodium stearoyl glutamate |  | 0.18 |
| Fragrance |  | 0.10 |
| Diameter of the globules of the oily phase (measured by quasi-elastic light scattering)* | at 24 h | >1 µm heterogeneous emulsion |
| Visual appearance |  | white |

*The measurement was performed using the BI-90 from Brookhaven.

This comparative example differs from the examples according to the invention in that the surfactant used, which is liquid and has an HLB of 13.7, does not contain at least 5 oxyethylenated groups.

2) Comparative Example 9

|  |  | Example 9 |
|---|---|---|
| PEG 8 isostearate | B | 6 |
| Hydrogenated polyisobutene |  | 13.5 |
| Apricot oil |  | 4.5 |
| Water |  | 0.144 |
| Water | D | 55.86 |
| Water | F | qs 100 |
| Disodium stearoyl glutamate |  | 0.12 |
| Diameter of the globules of the oily phase (measured by quasi-elastic light scattering)* | at 24 h | heterogeneous emulsion exhibiting oily globules with a diameter of more than a micron |
| Visual appearance |  | white |

*The measurement was performed using the BI-90 from Brookhaven.

Comparative Example 9 differs from the compositions of the invention in that the oily phase contains more than 15% by weight of oil containing triglycerides (apricot oil), since it contains 18.75% by weight of apricot oil relative to the weight of the oily phase. The emulsion obtained was heterogeneous and did not constitute a fine emulsion.

3) Comparative Example 10

|  |  | Example 10 |
|---|---|---|
| PEG 8 isostearate | B | 6 |
| Jojoba oil |  | 10 |
| Cyclopentasiloxane |  | 10 |
| Water |  | 2.5 |
| Water | D | 52 |
| Water | F | qs 100 |
| Disodium stearoyl glutamate |  | 0.10 |

Comparative Example 10 differs from the compositions of the invention in that the oily phase does not contain alkane. The obtained emulsion was not fine and presented oily globules having a size of some dozens of microns (ten microns or more), thus much greater than 500 nm.

The above written description of the invention provides a manner and process of making and using it such that any person skilled in this art is enabled to make and use the same, this enablement being provided in particular for the subject matter of the appended claims, which make up a part of the original description and including a composition for topical application in the form of an oil-in-water emulsion, comprising an oily phase dispersed in an aqueous phase, the globules of oil of which have a mean diameter ranging from 50 to 500 nm, wherein:

it contains an emulsifying system containing (i) at least one nonionic surfactant with a melting point of less than 45° C. and an HLB ranging from 10 to 15, the surfactant comprising a polar portion comprising at least 5 oxyethylene groups and an apolar portion comprising at least one branched or unsaturated alkyl chain containing from 14 to 22 carbon atoms, and (ii) at least one anionic surfactant, the oily phase contains oily constituents including at least one hydrocarbon-based oil with a molecular weight of greater than or equal to 400, the amount of hydrocarbon-based oils with a molecular weight of greater than or equal to 400 representing at least 25% by weight relative to the total weight of the oily phase and the amount of triglyceride-based oils representing less than 15% by weight relative to the total weight of the oily phase, wherein at least one hydrocarbon-based oil with a molecular weight of greater than or equal to 400 is chosen from alkanes with a melting point of less than 45° C., the weight ratio of the amount of oily constituents of the oily phase to the amount of emulsifying system ranges from 0.8 to 3.5.

As used above, the phrases "selected from the group consisting of," "chosen from," and the like include mixtures of the specified materials. Terms like "containing" etc. are open terms, meaning including at least.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition in the form of an oil-in-water emulsion, comprising an oily phase dispersed in an aqueous phase, globules of oil therein having a mean diameter ranging from 50 to 250 nm, wherein:
   the composition comprises an emulsifying system comprising (i) at least one nonionic surfactant which is liquid at a temperature of 45° C. and an HLB of 10-15, the nonionic surfactant comprising a polar portion comprising at least 5 oxyethylene groups and an apolar portion comprising at least one branched or unsaturated alkyl chain comprising from 14 to 22 carbon atoms, and (ii) at least one anionic surfactant,
   the oily phase comprises at least one hydrocarbon-based oil having a molecular weight of greater than or equal to 400, the amount of hydrocarbon-based oil(s) with a molecular weight of greater than or equal to 400 representing at least 25% by weight relative to the total weight of the oily phase and an amount of triglyceride-based oils representing 0-15% by weight relative to the total weight of the oily phase, wherein at least one hydrocarbon-based oil with a molecular weight of greater than or equal to 400 is selected from alkanes with a melting point of less than 45° C.,
   the weight ratio of the amount of oily constituents of the oily phase to the amount of emulsifying system is 0.8-3.5.

2. The composition according to claim 1, wherein the nonionic surfactant is selected from fatty acid esters of polyethylene glycol, oxyethylenated fatty acid esters of polyol and oxyethylenated fatty alcohol ethers, and mixtures thereof.

3. The composition according to claim 1, wherein the nonionic surfactant is chosen from PEG-8 isostearate, PEG-10 isostearate, PEG-12 isostearate, PEG-15 isostearate, PEG-15 glyceryl isostearate, PEG-20 sorbitan triisostearate and isosteareth-10, and mixtures thereof.

4. The composition according to claim 1, wherein the amount of nonionic surfactant(s) is 0.5% to 10% by weight relative to the total weight of the composition.

5. The composition according to claim 1, wherein the anionic surfactant is chosen from:
   alkaline salts of dicetyl and dimyristyl phosphate;
   alkaline salts of cholesteryl sulfate;
   alkaline salts of cholesteryl phosphate;
   acylamino acid salts;
   the sodium salts of phosphatidic acid;
   alkyl sulfates and alkylsulfonates;
   and mixtures thereof.

6. The composition according to claim 1, wherein the amount of anionic surfactant(s) is 0.05% to 2% by weight relative to the total weight of the composition.

7. The composition according to claim 1, wherein the amount of emulsifying system is 0.6%-11% by weight relative to the total weight of the composition.

8. The composition according to claim 1, wherein the hydrocarbon-based oil with a molecular weight of greater than or equal to 400 is chosen from fatty acid esters and fatty alcohol ethers, and mixtures thereof.

9. The composition according to claim 1, wherein the amount of oily phase is 0.5% to 55% by weight relative to the total weight of the composition.

10. The composition according to claim 1, wherein said composition is a skincare product, a hygiene product, a hair product, an antisun product or a makeup product.

11. A process for treating keratin material, comprising applying a composition according to claim 1 to keratin material.

12. An article comprising a water-insoluble substrate impregnated with a composition according to claim 1.

13. The article of claim 12, wherein said article is an article for caring for, removing makeup from, cleansing, or making up the skin, the lips and/or the eyelashes.

14. The composition according to claim 1, wherein the composition comprises at least one triglyceride-based oil.

15. The composition according to claim 1, wherein the oil globules have a mean diameter ranging from 80 to 200 nm.

16. The composition according to claim 1, wherein the amount of emulsifying system is 0.6%-9% by weight relative to the total weight of the composition.

* * * * *

UNITED STATES PATENT AND TRADEMARK OFFICE
CERTIFICATE OF CORRECTION

PATENT NO. : 8,741,322 B2
APPLICATION NO. : 11/154715
DATED : June 3, 2014
INVENTOR(S) : Odile Aubrun-Sonneville et al.

Page 1 of 1

It is certified that error appears in the above-identified patent and that said Letters Patent is hereby corrected as shown below:

In the Claims

Column 15, line 8, claim 1 "45°C." should read --45°C--
Column 15, line 24, claim 1 "45°C." should read --45°C--

Signed and Sealed this
Eighteenth Day of November, 2014

Michelle K. Lee
*Deputy Director of the United States Patent and Trademark Office*